United States Patent [19]
Wetterich et al.

[11] Patent Number: 5,847,194
[45] Date of Patent: Dec. 8, 1998

[54] CARBAMOYLCARBOXAMIDES

[75] Inventors: Frank Wetterich, Darmstadt; Oliver Wagner, Dexbach; Karl Eicken, Wachenheim; Eberhard Ammermann, Heppenheim; Gisela Lorenz, Hambach, all of Germany

[73] Assignee: BASF Aktiengesellschaft, Ludwigshafen, Germany

[21] Appl. No.: 793,447

[22] PCT Filed: Aug. 19, 1995

[86] PCT No.: PCT/EP95/03303

§ 371 Date: Mar. 3, 1997

§ 102(e) Date: Mar. 3, 1997

[87] PCT Pub. No.: WO96/07638

PCT Pub. Date: Mar. 14, 1996

[30] Foreign Application Priority Data

Sep. 3, 1994 [DE] Germany .......................... 44 31 467.1

[51] Int. Cl.[6] .................................................... C07C 26/00
[52] U.S. Cl. .............................. 560/28; 560/25; 562/455; 562/444; 562/443; 514/540; 514/542
[58] Field of Search ........................ 560/28, 25; 562/443, 562/444, 455; 514/540, 542

[56] References Cited

PUBLICATIONS

CA 115; 50298 Jan 8, 1990.

*Primary Examiner*—Paul J. Killos
*Attorney, Agent, or Firm*—Oblon. Spivak, McClelland, Maier & Neustadt, P.C.

[57] ABSTRACT

Carbamoylcarboxamides of the general formula I $$R^1-O-\underset{\underset{}{\|}}{C}-\underset{\underset{R^4}{|}}{N}-\underset{\underset{}{|}}{\overset{R^2}{C}}-\underset{\underset{}{\|}}{\overset{R^3}{C}}-\underset{\underset{}{|}}{N}-\left[\underset{\underset{X}{|}}{\overset{X}{C}}\right]_p\left[\underset{\underset{Y}{|}}{\overset{Y}{C}}\right]_q\text{(naphthyl)}-(R^6)_r \quad (I)$$

and their salts ($R^1$ is unsubstituted or substituted alkyl, alkenyl, alkynyl, cycloalkyl, cycloalkenyl or an unsubstituted or substituted nonaromatic carbo- or heterocycle;

$R^2$ is H or unhalogenated or halogenated alkyl or cycloalkyl;

$R^3$ is unsubstituted or substituted alkyl, cycloalkyl or phenylalkyl;

$R^4$ is H or one of the radicals $R^3$ or $R^3$ and $R^4$, together with the C atom to which they are bonded, are an unsubstituted or substituted carbo- or heterocycle;

$R^5$ independently of these is one of the radicals $R^2$;

X independently of one another is hydrogen, unsubstituted or substituted alkyl and/or alkenyl;

Y independently of one another and of these is one of the radicals X;

p,q independently of one another are 0, 1 or 2;

$R^6$ is halogen, cyano, nitro or unsubstituted or substituted alkyl, alkoxy, alkylthio or an unsubstituted or substituted phenyl group bonded via oxygen or sulfur;

r is 0, 1, 2 or 3), and compositions containing them, processes for preparation, and the use of the compounds I and the compositions are described.

7 Claims, No Drawings

CARBAMOYLCARBOXAMIDES

The present invention relates to carbamoylcarboxamides of the general formula I

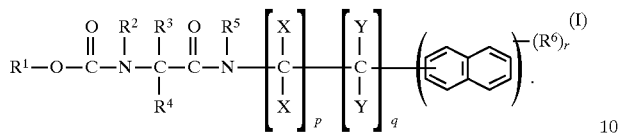

and their salts, where the variables have the following meanings:

$R^1$ is $C_1$–$C_8$-alkyl, $C_2$–$C_8$-alkenyl or $C_2$–$C_8$-alkynyl, it being possible for these radicals to be partially or completely halogenated and/or to carry one to three of the following groups: cyano, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalkyl, $C_3$–$C_7$-cycloalkenyl, aryl, aryloxy and heteroaryl, it being possible for the cyclic and aromatic rings of these groups to carry one to three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and heteroaryl, $C_3$–$C_7$-cycloalkyl or $C_3$–$C_7$-cycloalkenyl, it being possible for these radicals to be partially or completely halogenated and/or to carry one to three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being possible for the aromatic rings of these groups in turn to carry one to three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, a nonaromatic 4- to 8-membered ring which, as ring members, in addition to carbon can further contain one or two of the heteroatoms oxygen, sulfur and nitrogen, it being possible for the carbon atoms in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, and the second and any further nitrogen atom as a heteroatom in the ring carrying hydrogen or a $C_1$–$C_4$-alkyl group;

$R^2$ is hydrogen, or $C_1$–$C_8$-alkyl or $C_3$–$C_7$-cycloalkyl which can be partially or completely halogenated;

$R^3$ is $C_1$–$C_8$-alkyl, it being possible for this radical to carry one to three of the following groups: halogen, cyano, $C_1$–$C_4$-alkoxy, $C_1$–$C_4$-haloalkoxy, $C_1$–$C_4$-alkylthio and $C_1$–$C_4$-alkoxycarbonyl, $C_3$–$C_7$-cycloalkyl or phenyl-($C_1$–$C_4$)-alkyl, it being possible for the rings of these radicals to carry one to three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

$R^4$ is hydrogen or one of the radicals $R^3$ or $R^3$ and $R^4$, together with the C atom to which they are bonded, are a 4- to 8-membered ring which, as ring members, in addition to carbon can further contain one or two of the heteroatoms oxygen, sulfur and nitrogen, it being possible for the carbon atoms in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, and nitrogen as a heteroatom carrying hydrogen or a $C_1$–$C_4$-alkyl group;

$R^5$ independently of these is one of the radicals $R^2$;

X independently of one another is hydrogen, $C_1$–$C_8$-alkyl and/or $C_2$–$C_8$-alkenyl, it being possible for these radicals to be partially or completely halogenated and/or to carry one to three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy;

Y independently of one another and of these is one of the radicals X;

p,q independently of one another are 0, 1 or 2;

$R^6$ is halogen, cyano, nitro, $C_1$–$C_8$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio or a phenyl group bonded via oxygen or sulfur, which is unsubstituted or can carry one to three of the following substituents: halogen, $C_1$–$C_4$-alkyl or $C_1$–$C_4$-alkoxy, where $R^6$ for r>1 can be various radicals from those mentioned;

r is 0, 1, 2 or 3.

The invention additionally relates to processes for preparing the compounds I. The invention furthermore relates to compositions which contain the compounds I or their salts, a method of preparing compositions of this type and a method for controlling harmful fungi and the use of the compounds I, their salts or the compositions therefor.

Compounds of type I having fungicidal action have already been disclosed in the following publications: in particular EP-A 554 729 and DE-A 43 21 897, in addition EP-A 398 072, EP-A 425 925, EP-A 472 996, EP-A 477 639, EP-A 485 794, EP-A 493 683, EP-A 496 239, EP-A 550 788 and EP-A 587 110). However, the known compounds are still not satisfactory with respect to their fungicidal action.

It is an object of the present invention to provide novel carbamoylcarboxamides having an improved action against harmful fungi.

We have now found that this object is achieved by the compounds I defined at the outset, their salts and compositions containing them.

We have furthermore found processes for preparing the compounds I and the compositions containing them and additionally a method of controlling harmful fungi and the use of the compounds I, their salts or the compositions therefor.

The subject matter of German Patent Application P 44 31 467.1 which is relevant to the present invention is hereby included.

The compounds I can be prepared in a manner known per se starting from the corresponding carbamoylcarboxylic acids II. The compounds I are preferably obtained by the processes A and B described in the following (the Houben-Weyl literature citations relate to: Houben-Weyl, Methoden der Organischen Chemie (Methods of Organic Chemistry), 4th edition, Thieme Verlag, Stuttgart).

Process A

The carbamoylcarboxamides I are obtained by reacting carbamoylcarboxylic acids II with the amines III.

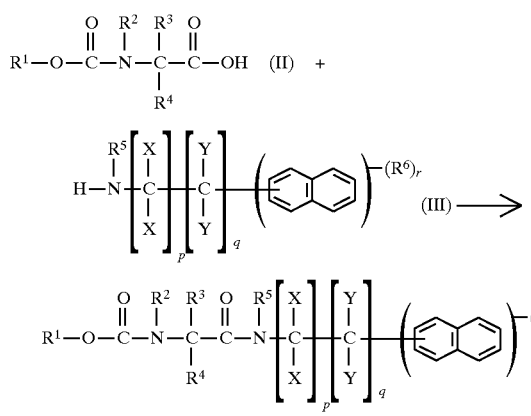

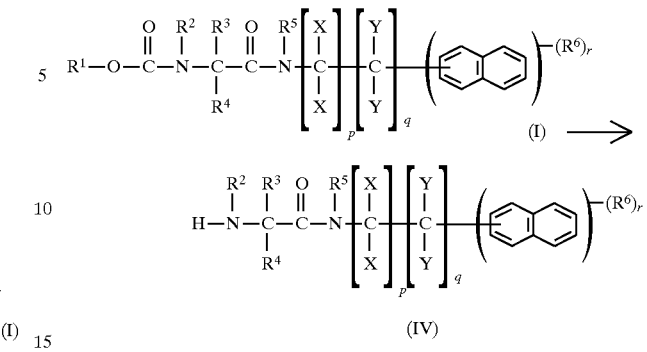

The carbamoylcarboxylic acids II are known or can be prepared by known methods, especially starting from the amino acids on which they are based (cf. Houben-Weyl, Volume 15/1, page 46 to page 305, especially page 117 to page 125).

The amines III are likewise known or can be easily obtained (cf. Organikum, VEB Deutscher Verlag der Wissenschaften, 15th edition, Berlin, 1977, page 610 ff.; Houben-Weyl, Volume 15/1, page 648–665; Indian J. Chem. 10 (1972), page 366).

This process A is preferably carried out in such a way that the carbamoylcarboxylic acids II are first converted to carboxyl-activated derivatives, especially to acyl cyanides or anhydrides (cf. Tetrahedron Letters, Volume 18 (1973), page 1595 to page 1598, or Houben-Weyl, Volume 15/1, page 28 to page 32). These derivatives are then reacted with the amines III in the presence of bases.

A suitable reaction for preparing the carboxyl-activated acyl cyanides is eg. the reaction of the carbamoylcarboxylic acids II with diethyl cyanophosphonate, especially in an inert solvent such as tetrahydrofuran or toluene.

To prepare the carboxyl-activated anhydrides, the reaction of the carbamoylcarboxylic acid II with carbonyl chlorides such as isobutyl chloroformate in the presence of bases and if appropriate in an inert solvent such as toluene or tetrahydrofuran is preferred.

The reaction of the amines III with the carboxyl-activated carbamoylcarboxylic acids II is preferably carried out in a solvent such as dichloromethane, tetrahydrofuran or toluene.

The bases used can in particular be the amines III themselves, the latter customarily being recovered from the crude product.

In a preferred embodiment of this process step, the carbamoylcarboxylic acid II, the amine III, the reagent suitable for the production of the carboxyl-activated derivative of the carbamoylcarboxylic acid II and the base are reacted in a one-pot process, if appropriate in an inert solvent, and the crude product is then worked up to the carbamoylcarboxamide I in a manner known per se.

Process B

The carbamoylcarboxamides I are obtained by converting the carbamoylcarboxamides I in which the group $R^1$—O—(CO) is a protective group which can be removed in a manner known per se to amino acid amides IV and reacting these with chloroformic acid ester V in the presence of a base.

Step Ba: Preparation of the amino acid amides IV

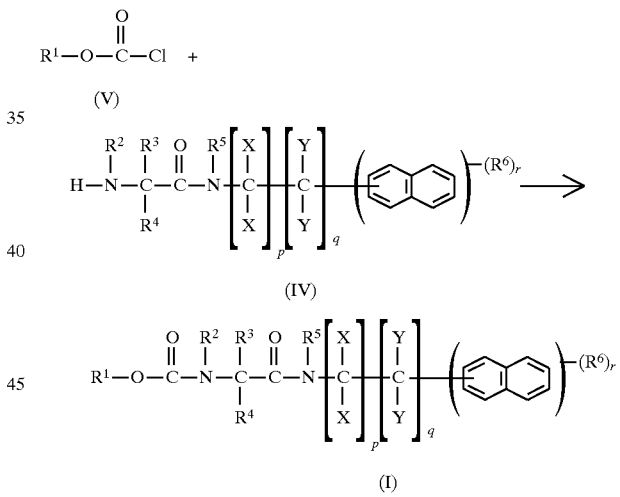

The removal of the group $R^1$—O—(CO) from the carbamoylcarboxamides I can be carried out in a manner known per se (cf. Houben-Weyl, Volume 15/1, page 46 to page 305, especially page 126 to page 129).

Suitable removable groups contain, as the $R^1$ radical, a tert-butyl group or the benzyl group.

If $R^1$=tert-butyl, for example, removal is customarily carried out by reaction with an acid, in particular a protic acid such as eg. hydrochloric acid or trifluoroacetic acid (ibid., page 126 to page 129).

The carbamoylcarboxamides I suitable as starting substances can be obtained by known processes (cf. Houben-Weyl, Volume 15/1, page 28 to page 32) or in particular by process A according to the invention.

Step Bb: Preparation of the carbamoylcarboxamides I

The amino acid amides IV resulting from the synthesis step (Ba) are reacted with the chloroformic acid esters V in the presence of bases.

The chloroformic acid esters V are generally known or can be prepared by known processes.

The reaction is preferably carried out in an organic solvent, especially toluene, methylene chloride or tetrahydrofuran, or mixtures of these.

Suitable bases are equally inorganic and organic bases, organic bases and among them, in turn, tertiary amines such as triethylamine, pyridine and N-methylpiperidine being preferred.

As a rule, the reaction is carried out at from −40° to 50° C., preferably from −10° to 20° C.

Otherwise, the carrying-out of this reaction is familiar to the person skilled in the art, so no further details are needed therefor (cf. Houben-Weyl, Volume 15/1, page 117 to page 139).

The reaction mixtures obtained by processes A and B are worked up in a customary manner, eg. by mixing with water, separating the phases and where appropriate chromatographically purifying the crude products. The intermediate and final products are in some cases obtained in the form of colorless or slightly brownish, viscous oils, which can be freed from volatile constituents under reduced pressure and at moderately elevated temperature. If the intermediates and final products are obtained as solids, the purification can also be carried out, for example, by recrystallizing or digesting.

Depending on the nature of the substituents, where appropriate the compounds of the formula I can be obtained as geometric and/or optical isomers or isomer mixtures. Both the pure isomers and the mixtures of the isomers have fungicidal action.

Also part of the invention are the salts, especially of the acid-stable compounds I which contain basic centers, especially basic nitrogen atoms, in particular with mineral acids such as sulfuric acid and phosphoric acid or Lewis acids such as zinc chloride. Customarily, in this case the nature of the salt does not matter. In the context of the invention those salts are preferred which do not harm the plants, surfaces, materials or spaces to be kept free from harmful fungi and do not adversely affect the action of the compounds I. Agriculturally utilizable salts of this type are particularly important.

The salts of the compounds I are accessible in a manner known per se, especially by reacting the corresponding carbamoylcarboxamides I with said acids in water or an inert organic solvent at from −80° to 120° C., preferably 0° to 60° C.

As a rule, the preparation of the salts is independent of the pressure, which is why the reaction is especially carried out at atmospheric pressure.

In the definition of the compounds I given at the outset, collective terms were used which are representative of the following substituents:

halogen: fluorine, chlorine, bromine and iodine;

alkyl: straight-chain or branched alkyl groups having 1 to 8 carbon atoms, eg. $C_1$–$C_6$-alkyl such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 1,1-dimethylpropyl, 2,2-dimethylpropyl, 1,2-dimethylpropyl, 1-ethylpropyl, n-hexyl, r-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, 1,3-dimethylbutyl, 2,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl or partially or completely halogenated alkyl: straight-chain or branched alkyl groups having 1 to 4 or 8 carbon atoms (as mentioned above), it being possible in these groups for the hydrogen atoms to be partially or completely replaced by halogen atoms (as mentioned above), eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkoxy groups having 1 to 4 carbon atoms, eg. $C_1$–$C_3$-alkoxy such as methoxy, ethoxy, propoxy and 1-methylethoxy;

alkoxyalkyl: straight-chain or branched alkyl groups having 1 to 8 carbon atoms (as mentioned above) which, in any desired position, carry a straight-chain or branched alkoxy group (as mentioned above), having, in the case of $C_1$–$C_4$-alkoxyalkyl, 1 to 4 carbon atoms, such as methoxymethyl, ethoxymethyl, n-propoxymethyl, n-butoxymethyl, 1-methoxyethyl, 2-methoxyethyl, 1-ethoxyethyl, 2-ethoxyethyl, 2-n-propoxyethyl and 2-butoxyethyl;

haloalkoxy: straight-chain or branched alkoxy groups having 1 to 4 carbon atoms (as mentioned above), it being possible in these groups for the hydrogen atoms to be partially or completely replaced by halogen atoms (as mentioned above), eg. $C_1$–$C_2$-haloalkoxy such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy;

alkylthio: straight-chain or branched alkyl groups having 1 to 4 carbon atoms (as mentioned above) which are bonded to the structure via a sulfur atom (—S—), eg. $C_1$–$C_4$-alkylthio such as methylthio, ethylthio, propylthio, 1-methylethylthio, n-butylthio and tert-butylthio; alkoxycarbonyl: straight-chain or branched alkoxy groups having 1 to 4 C atoms (as mentioned above), which are bonded to the structure via a carbonyl group (—CO—);

alkenyl: straight-chain or branched alkenyl groups having 2 to 8 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 2-methyl-1-propenyl, 1-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1, 2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched alkynyl groups having 2 to 8 carbon atoms and a triple bond in any desired position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic alkyl groups having 3 to 7 carbon ring members, eg. $C_3$–$C_7$-cycloalkyl such as cyclopropyl, cyclobutyl, cyclopentyl, cyclohexyl and cycloheptyl;

cycloalkenyl: monocyclic alkyl groups having 5 to 7 carbon ring members which contain one or more double bonds, eg. $C_5$–$C_7$-cycloalkenyl such as cyclopentenyl, cyclohexenyl and cycloheptenyl;

nonaromatic 4- to 8-membered rings which, as ring members, in addition to carbon further contain one or two oxygen, sulfur or nitrogen atoms, such as saturated 5- or 6-membered rings having 1 or 2 nitrogen and/or oxygen atoms such as 3-tetrahydrofuranyl, 1-piperidinyl, 2-piperidinyl, 3-piperidinyl, 4-piperidinyl, 2-tetrahydropyranyl, 3-tetrahydropyranyl, 4-tetrahydropyranyl, 2-morpholinyl and 3-morpholinyl;

aryl: monocyclic or polycyclic aromatic groups having 6 to 10 C atoms such as phenyl and naphthyl;

arylalkyl: aryl groups (as mentioned above) which in the case of aryl-($C_1$–$C_4$)-alkyl are bonded to the structure via alkyl groups having 1 to 4 carbon atoms (as mentioned above), eg. phenyl-($C_1$–$C_4$)-alkyl such as benzyl, 2-phenylethyl, 3-phenylpropyl, 4-phenylbutyl, 1-phenylethyl, 1-phenylpropyl and 1-phenylbutyl;

aryloxy: aryl groups (as mentioned above) which are bonded to the structure via an oxygen atom (—O—), such as phenoxy, 1-naphthoxy and 2-naphthoxy;

heteroaryl: aromatic mono- or polycyclic radicals which in addition to carbon ring members can additionally contain 1 to 4 nitrogen atoms or 1 to 3 nitrogen atoms and an oxygen or a sulfur atom or an oxygen or a sulfur atom, eg.:

5-membered heteroaryl, containing 1 to 3 nitrogen atoms: 5-membered ring heteroaryl groups which in addition to carbon atoms can contain 1 to 3 nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl, containing 1 to 4 nitrogen atoms or 1 to 3 nitrogen atoms and 1 sulfur or oxygen atom or 1 oxygen or sulfur atom: 5-membered ring heteroaryl groups which in addition to carbon atoms can contain 1 to 4 nitrogen atoms or 1 to 3 nitrogen atoms and 1 sulfur or oxygen atom or 1 oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, containing 1 to 3 nitrogen atoms or 1 nitrogen atom and/or an oxygen or sulfur atom: 5-membered ring heteroaryl groups which in addition to carbon atoms can contain 1 to 4 nitrogen atoms or 1 to 3 nitrogen atoms and 1 sulfur or oxygen atom or 1 oxygen or sulfur atom as ring members, and in which 2 adjacent carbon ring members or 1 nitrogen and 1 adjacent carbon ring member can be bridged by a buta-1,3-diene-1,4-diyl group;

5-membered heteroaryl bonded via nitrogen and containing 1 to 4 nitrogen atoms, or benzo-fused 5-membered heteroaryl bonded via nitrogen and containing 1 to 3 nitrogen atoms: 5-membered ring heteroaryl groups which in addition to carbon atoms can contain 1 to 4 nitrogen atoms or 1 to 3 nitrogen atoms as ring members, and in which 2 adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl, containing 1 to 3 or 1 to 4 nitrogen atoms: 6-membered ring heteroaryl groups which in addition to carbon atoms can contain 1 to 3 or 1 to 4 nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl, containing 1 to 4 nitrogen atoms: 6-membered ring heteroaryl groups in which 2 adjacent carbon ring members can be bridged by a buta-1,3-diene-1,4-diyl group, eg. quinoline, isoquinoline, quinazoline and quinoxaline.

The statement partially or completely halogenated is intended to express that in the groups characterized in this way the hydrogen atoms can be partially or completely replaced by identical or different halogen atoms, as mentioned above.

With respect to their action against harmful fungi, compounds I are preferred in which the radicals have the following meanings, to be specific on their own per se or in combination. The groups mentioned in the meanings of radicals in the following can also be substituted according to the claims.

$R^1$ is $C_1$–$C_8$-alkyl and especially $C_1$–$C_4$-alkyl;

$R^2$ is hydrogen or $C_1$–$C_8$-alkyl;

$R^3$ is $C_1$–$C_8$-alkyl, $C_3$–$C_7$-cycloalkyl or phenyl-($C_1$–$C_4$)-alkyl, especially $C_1$–$C_8$-alkyl and in particular $C_3$-alkyl, preferably isopropyl;

$R^4$ is $C_1$–$C_8$-alkyl and especially hydrogen;

$R^5$ is hydrogen;

X independently of one another is hydrogen or $C_1$–$C_8$-alkyl, preferably $C_1$–$C_8$-alkyl, especially $C_1$–$C_4$-alkyl;

Y independently of one another is hydrogen or $C_1$–$C_8$-alkyl, especially hydrogen;

p is 0 or 1, especially 1;

q is 0 or 1, especially 0;

$R^6$ is halogen or $C_1$–$C_8$-alkyl, especially halogen [sic] or $C_1$–$C_4$-alkyl;

r is 0 or 1, especially 0.

With respect to their use, the compounds I compiled in the following Tables 1 to 5 are very particularly preferred.

TABLE 1

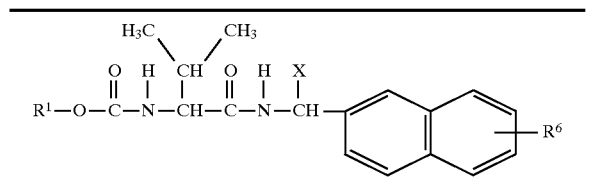

| No. | R$^1$ | X | R$^6$ |
|---|---|---|---|
| 1.2 | C(CH$_3$)$_3$ | CH$_2$CH$_3$ | H |
| 1.3 | C(CH$_3$)$_3$ | CH$_3$ | 1-Cl |
| 1.4 | C(CH$_3$)$_3$ | CH$_3$ | 3-Cl |
| 1.5 | C(CH$_3$)$_3$ | CH$_3$ | 4-Cl |
| 1.6 | C(CH$_3$)$_3$ | CH$_3$ | 5-Cl |
| 1.7 | C(CH$_3$)$_3$ | CH$_3$ | 6-Cl |
| 1.8 | C(CH$_3$)$_3$ | CH$_3$ | 7-Cl |
| 1.9 | C(CH$_3$)$_3$ | CH$_3$ | 8-Cl |
| 1.10 | C(CH$_3$)$_3$ | CH$_3$ | 1-OCH$_3$ |
| 1.11 | C(CH$_3$)$_3$ | CH$_3$ | 3-OCH$_3$ |
| 1.12 | C(CH$_3$)$_3$ | CH$_3$ | 4-OCH$_3$ |
| 1.13 | C(CH$_3$)$_3$ | CH$_3$ | 5-OCH$_3$ |
| 1.14 | C(CH$_3$)$_3$ | CH$_3$ | 6-OCH$_3$ |
| 1.15 | C(CH$_3$)$_3$ | CH$_3$ | 7-OCH$_3$ |
| 1.16 | C(CH$_3$)$_3$ | CH$_3$ | 5,6-(OCH$_3$)$_2$ |
| 1.17 | C(CH$_3$)$_3$ | CH$_3$ | 5,7-(OCH$_3$)$_2$ |
| 1.18 | C(CH$_3$)$_3$ | CH$_3$ | 1-CH$_3$ |
| 1.19 | C(CH$_3$)$_3$ | CH$_3$ | 3-CH$_3$ |
| 1.20 | C(CH$_3$)$_3$ | CH$_3$ | 4-CH$_3$ |
| 1.21 | C(CH$_3$)$_3$ | CH$_3$ | 5-CH$_3$ |
| 1.23 | C(CH$_3$)$_3$ | CH$_3$ | 7-CH$_3$ |
| 1.24 | C(CH$_3$)$_3$ | CH$_3$ | 5,6-(CH$_3$)$_2$ |
| 1.25 | C(CH$_3$)$_3$ | CH$_3$ | 5,7-(CH$_3$)$_2$ |
| 1.26 | C(CH$_3$)$_3$ | CH$_3$ | 1-OH |
| 1.28 | CH(CH$_3$)$_2$ | CH$_2$CH$_3$ | H |
| 1.29 | CH(CH$_3$)$_2$ | CH$_3$ | 1-Cl |
| 1.30 | CH(CH$_3$)$_2$ | CH$_3$ | 3-Cl |
| 1.31 | CH(CH$_3$)$_2$ | CH$_3$ | 4-Cl |
| 1.32 | CH(CH$_3$)$_2$ | CH$_3$ | 5-Cl |
| 1.33 | CH(CH$_3$)$_2$ | CH$_3$ | 6-Cl |
| 1.34 | CH(CH$_3$)$_2$ | CH$_3$ | 7-Cl |
| 1.35 | CH(CH$_3$)$_2$ | CH$_3$ | 8-Cl |
| 1.36 | CH(CH$_3$)$_2$ | CH$_3$ | 1-OCH$_3$ |
| 1.37 | CH(CH$_3$)$_2$ | CH$_3$ | 3-OCH$_3$ |
| 1.38 | CH(CH$_3$)$_2$ | CH$_3$ | 4-OCH$_3$ |
| 1.39 | CH(CH$_3$)$_2$ | CH$_3$ | 5-OCH$_3$ |
| 1.41 | CH(CH$_3$)$_2$ | CH$_3$ | 7-OCH$_3$ |
| 1.42 | CH(CH$_3$)$_2$ | CH$_3$ | 5,6-(OCH$_3$)$_2$ |
| 1.43 | CH(CH$_3$)$_2$ | CH$_3$ | 5,7-(OCH$_3$)$_2$ |
| 1.44 | CH(CH$_3$)$_2$ | CH$_3$ | 1-CH$_3$ |
| 1.45 | CH(CH$_3$)$_2$ | CH$_3$ | 3-CH$_3$ |
| 1.46 | CH(CH$_3$)$_2$ | CH$_3$ | 4-CH$_3$ |
| 1.47 | CH(CH$_3$)$_2$ | CH$_3$ | 5-CH$_3$ |
| 1.49 | CH(CH$_3$)$_2$ | CH$_3$ | 7-CH$_3$ |
| 1.50 | CH(CH$_3$)$_2$ | CH$_3$ | 5,6-(CH$_3$)$_2$ |
| 1.51 | CH(CH$_3$)$_2$ | CH$_3$ | 5,7-(CH$_3$)$_2$ |
| 1.52 | CH(CH$_3$)$_2$ | CH$_3$ | 1-OH |
| 1.54 | CH(CH$_3$)(C$_2$H$_5$) | CH$_2$CH$_3$ | H |
| 1.55 | CH(CH$_3$)(C$_2$H$_5$) | CH$_3$ | 1-Cl |
| 1.56 | CH(CH$_3$)(C$_2$H$_5$) | CH$_3$ | 3-Cl |
| 1.57 | CH(CH$_3$)(C$_2$H$_5$) | CH$_3$ | 4-Cl |
| 1.58 | CH(CH$_3$)(C$_2$H$_5$) | CH$_3$ | 5-Cl |
| 1.59 | CH(CH$_3$)(C$_2$H$_5$) | CH$_3$ | 6-Cl |
| 1.60 | CH(CH$_3$)(C$_2$H$_5$) | CH$_3$ | 7-Cl |
| 1.61 | CH(CH$_3$)(C$_2$H$_5$) | CH$_3$ | 8-Cl |
| 1.62 | CH(CH$_3$)(C$_2$H$_5$) | CH$_3$ | 1-OCH$_3$ |
| 1.63 | CH(CH$_3$)(C$_2$H$_5$) | CH$_3$ | 3-OCH$_3$ |
| 1.64 | CH(CH$_3$)(C$_2$H$_5$) | CH$_3$ | 4-OCH$_3$ |
| 1.65 | CH(CH$_3$)(C$_2$H$_5$) | CH$_3$ | 5-OCH$_3$ |
| 1.66 | CH(CH$_3$)(C$_2$H$_5$) | CH$_3$ | 6-OCH$_3$ |
| 1.67 | CH(CH$_3$)(C$_2$H$_5$) | CH$_3$ | 7-OCH$_3$ |
| 1.68 | CH(CH$_3$)(C$_2$H$_5$) | CH$_3$ | 5,6-(OCH$_3$)$_2$ |
| 1.69 | CH(CH$_3$)(C$_2$H$_5$) | CH$_3$ | 5,7-(OCH$_3$)$_2$ |
| 1.70 | CH(CH$_3$)(C$_2$H$_5$) | CH$_3$ | 1-CH$_3$ |
| 1.71 | CH(CH$_3$)(C$_2$H$_5$) | CH$_3$ | 3-CH$_3$ |
| 1.72 | CH(CH$_3$)(C$_2$H$_5$) | CH$_3$ | 4-CH$_3$ |

TABLE 1-continued

| No. | R$^1$ | X | R$^6$ |
|---|---|---|---|
| 1.73 | CH(CH$_3$)(C$_2$H$_5$) | CH$_3$ | 5-CH$_3$ |
| 1.75 | CH(CH$_3$)(C$_2$H$_5$) | CH$_3$ | 7-CH$_3$ |
| 1.76 | CH(CH$_3$)(C$_2$H$_5$) | CH$_3$ | 5,6-(CH$_3$)$_2$ |
| 1.77 | CH(CH$_3$)(C$_2$H$_5$) | CH$_3$ | 5,7-(CH$_3$)$_2$ |
| 1.78 | CH(CH$_3$)(C$_2$H$_5$) | CH$_3$ | 1-OH |
| 1.79 | C(CH$_3$)$_3$ | CH$_3$ | 6-CN |
| 1.80 | CH(CH$_3$)$_2$ | CH$_3$ | 6-CN |
| 1.81 | CH(CH$_3$)(C$_2$H$_5$) | CH$_3$ | 6-CN |
| 1.82 | C(CH$_3$)$_3$ | CH$_3$ | 5-CN |
| 1.83 | CH(CH$_3$)$_2$ | CH$_3$ | 5-CN |
| 1.84 | CH(CH$_3$)C$_2$H$_5$ | CH$_3$ | 5-CN |

TABLE 2

| No. | R$^1$ | X | R$^6$ |
|---|---|---|---|
| 2.2 | C(CH$_3$)$_3$ | CH$_2$CH$_3$ | H |
| 2.3 | C(CH$_3$)$_3$ | CH$_3$ | 2-Cl |
| 2.4 | C(CH$_3$)$_3$ | CH$_3$ | 3-Cl |
| 2.6 | C(CH$_3$)$_3$ | CH$_3$ | 5-Cl |
| 2.7 | C(CH$_3$)$_3$ | CH$_3$ | 6-Cl |
| 2.8 | C(CH$_3$)$_3$ | CH$_3$ | 7-Cl |
| 2.9 | C(CH$_3$)$_3$ | CH$_3$ | 8-Cl |
| 2.10 | C(CH$_3$)$_3$ | CH$_3$ | 2-OCH$_3$ |
| 2.11 | C(CH$_3$)$_3$ | CH$_3$ | 3-OCH$_3$ |
| 2.12 | C(CH$_3$)$_3$ | CH$_3$ | 4-OCH$_3$ |
| 2.13 | C(CH$_3$)$_3$ | CH$_3$ | 5-OCH$_3$ |
| 2.14 | C(CH$_3$)$_3$ | CH$_3$ | 6-OCH$_3$ |
| 2.15 | C(CH$_3$)$_3$ | CH$_3$ | 7-OCH$_3$ |
| 2.16 | C(CH$_3$)$_3$ | CH$_3$ | 5,6-(OCH$_3$)$_2$ |
| 2.17 | C(CH$_3$)$_3$ | CH$_3$ | 5,7-(OCH$_3$)$_2$ |
| 2.18 | C(CH$_3$)$_3$ | CH$_3$ | 2-CH$_3$ |
| 2.19 | C(CH$_3$)$_3$ | CH$_3$ | 3-CH$_3$ |
| 2.20 | C(CH$_3$)$_3$ | CH$_3$ | 4-CH$_3$ |
| 2.21 | C(CH$_3$)$_3$ | CH$_3$ | 5-CH$_3$ |
| 2.22 | C(CH$_3$)$_3$ | CH$_3$ | 6-CH$_3$ |
| 2.23 | C(CH$_3$)$_3$ | CH$_3$ | 7-CH$_3$ |
| 2.24 | C(CH$_3$)$_3$ | CH$_3$ | 5,6-(CH$_3$)$_2$ |
| 2.25 | C(CH$_3$)$_3$ | CH$_3$ | 5,7-(CH$_3$)$_2$ |
| 2.26 | C(CH$_3$)$_3$ | CH$_3$ | 2-OH |
| 2.28 | CH(CH$_3$)$_2$ | CH$_2$CH$_3$ | H |
| 2.29 | CH(CH$_3$)$_2$ | CH$_3$ | 2-Cl |
| 2.30 | CH(CH$_3$)$_2$ | CH$_3$ | 3-Cl |
| 2.32 | CH(CH$_3$)$_2$ | CH$_3$ | 5-Cl |
| 2.33 | CH(CH$_3$)$_2$ | CH$_3$ | 6-Cl |
| 2.34 | CH(CH$_3$)$_2$ | CH$_3$ | 7-Cl |
| 2.35 | CH(CH$_3$)$_2$ | CH$_3$ | 8-Cl |
| 2.36 | CH(CH$_3$)$_2$ | CH$_3$ | 2-OCH$_3$ |
| 2.37 | CH(CH$_3$)$_2$ | CH$_3$ | 3-OCH$_3$ |
| 2.38 | CH(CH$_3$)$_2$ | CH$_3$ | 4-OCH$_3$ |
| 2.39 | CH(CH$_3$)$_2$ | CH$_3$ | 5-OCH$_3$ |
| 2.40 | CH(CH$_3$)$_2$ | CH$_3$ | 6-OCH$_3$ |
| 2.41 | CH(CH$_3$)$_2$ | CH$_3$ | 7-OCH$_3$ |
| 2.42 | CH(CH$_3$)$_2$ | CH$_3$ | 5,6-(OCH$_3$)$_2$ |
| 2.43 | CH(CH$_3$)$_2$ | CH$_3$ | 5,7-(OCH$_3$)$_2$ |
| 2.44 | CH(CH$_3$)$_2$ | CH$_3$ | 2-CH$_3$ |
| 2.45 | CH(CH$_3$)$_2$ | CH$_3$ | 3-CH$_3$ |
| 2.46 | CH(CH$_3$)$_2$ | CH$_3$ | 4-CH$_3$ |

TABLE 2-continued $$R^1-O-\overset{O}{\underset{\|}{C}}-\overset{H}{\underset{|}{N}}-\overset{H_3C\diagdown\diagup CH_3}{\underset{|}{CH}}-\overset{O}{\underset{\|}{C}}-\overset{H}{\underset{|}{N}}-\overset{X}{\underset{|}{CH}}-\text{(naphthyl)}-R^6$$

| No. | R¹ | X | R⁶ |
|---|---|---|---|
| 2.47 | CH(CH₃)₂ | CH₃ | 5-CH₃ |
| 2.48 | CH(CH₃)₂ | CH₃ | 6-CH₃ |
| 2.49 | CH(CH₃)₂ | CH₃ | 7-CH₃ |
| 2.50 | CH(CH₃)₂ | CH₃ | 5,6-(CH₃)₂ |
| 2.51 | CH(CH₃)₂ | CH₃ | 5,7-(CH₃)₂ |
| 2.52 | CH(CH₃)₂ | CH₃ | 2-OH |
| 2.54 | CH(CH₃)(C₂H₅) | CH₂CH₃ | H |
| 2.55 | CH(CH₃)(C₂H₅) | CH₃ | 2-Cl |
| 2.56 | CH(CH₃)(C₂H₅) | CH₃ | 3-Cl |
| 2.58 | CH(CH₃)(C₂H₅) | CH₃ | 5-Cl |
| 2.59 | CH(CH₃)(C₂H₅) | CH₃ | 6-Cl |
| 2.60 | CH(CH₃)(C₂H₅) | CH₃ | 7-Cl |
| 2.61 | CH(CH₃)(C₂H₅) | CH₃ | 8-Cl |
| 2.62 | CH(CH₃)(C₂H₅) | CH₃ | 2-OCH₃ |
| 2.63 | CH(CH₃)(C₂H₅) | CH₃ | 3-OCH₃ |
| 2.64 | CH(CH₃)(C₂H₅) | CH₃ | 4-OCH₃ |
| 2.65 | CH(CH₃)(C₂H₅) | CH₃ | 5-OCH₃ |
| 2.66 | CH(CH₃)(C₂H₅) | CH₃ | 6-OCH₃ |
| 2.67 | CH(CH₃)(C₂H₅) | CH₃ | 7-OCH₃ |
| 2.68 | CH(CH₃)(C₂H₅) | CH₃ | 5,6-(OCH₃)₂ |
| 2.69 | CH(CH₃)(C₂H₅) | CH₃ | 5,7-(OCH₃)₂ |
| 2.70 | CH(CH₃)(C₂H₅) | CH₃ | 2-CH₃ |
| 2.71 | CH(CH₃)(C₂H₅) | CH₃ | 3-CH₃ |
| 2.72 | CH(CH₃)(C₂H₅) | CH₃ | 4-CH₃ |
| 2.73 | CH(CH₃)(C₂H₅) | CH₃ | 5-CH₃ |
| 2.74 | CH(CH₃)(C₂H₅) | CH₃ | 6-CH₃ |
| 2.75 | CH(CH₃)(C₂H₅) | CH₃ | 7-CH₃ |
| 2.76 | CH(CH₃)(C₂H₅) | CH₃ | 5,6-(CH₃)₂ |
| 2.77 | CH(CH₃)(C₂H₅) | CH₃ | 5,7-(CH₃)₂ |
| 2.78 | CH(CH₃)(C₂H₅) | CH₃ | 2-OH |

TABLE 3

$$R^1-O-\overset{O}{\underset{\|}{C}}-\overset{H}{\underset{|}{N}}-\overset{H_3C\diagdown\diagup CH_3}{\underset{|}{CH}}-\overset{O}{\underset{\|}{C}}-\overset{H}{\underset{|}{N}}-\overset{X}{\underset{|}{CH}}-\overset{Y}{\underset{|}{CH}}-\text{(naphthyl)}$$

| No. | R¹ | X | Y |
|---|---|---|---|
| 3.1 | C(CH₃)₃ | H | H |
| 3.3 | C(CH₃)₃ | H | CH₃ |
| 3.4 | CH(CH₃)₂ | H | H |
| 3.6 | CH(CH₃)₂ | H | CH₃ |
| 3.7 | CH(CH₃)(C₂H₅) | H | H |
| 3.8 | CH(CH₃)(C₂H₅) | CH₃ | H |
| 3.9 | CH(CH₃)(C₂H₅) | H | CH₃ |

The novel compounds of the formula I and their salts are suitable for controlling harmful fungi.

The novel compounds or their salts can be applied by spraying, atomizing, dusting, scattering or watering, for example in the form of directly sprayable solutions, powders, suspensions, even high-percentage aqueous, oily or other suspensions or dispersions, emulsions, oil dispersions, pastes, dusting compositions, scattering compositions or granules. The application forms depend on the intended uses; in each case they should if possible ensure the finest dispersion of the active compounds according to the invention.

Normally, in the treatment of plants the plants are sprayed or dusted with the active compounds or the seeds of the plants are treated with the active compounds.

The formulations are prepared in a known manner, eg. by extending the active compound with solvents and/or carriers, if desired using emulsifiers and dispersants, where if water is used as a diluent other organic solvents can also be used as auxiliary solvents. Suitable auxiliaries for this purpose are mainly: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, aluminas, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as ligninsulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol-ether, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol- or tributylphenylpolyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, scattering and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers.

Examples of such preparations are:
I. a solution of 90 parts by weight of a compound I according to the invention and 10 parts by weight of N-methyl-2-pyrrolidone, which is suitable for application in the form of very small drops;
II. a mixture of 10 parts by weight of a compound I according to the invention, 70 parts by weight of xylene, 10 parts by weight of the addition product of from 8 to 10 mol of ethylene oxide to 1 mol of oleic acid N-monoethanolamide, 5 parts by weight of calcium salt of dodecylbenzene-sulfonic acid, 5 parts by weight of the addition product of 40 mol of ethylene oxide to 1 mol of castor oil; a dispersion is obtained by finely dispersing the solution in water.
III. an aqueous dispersion of 10 parts by weight of a compound I according to the invention, 40 parts by weight of cyclohexanone, 30 parts by weight of isobutanol, 20 parts by weight of the addition product of 40 mol of ethylene oxide to 1 mol of castor oil;

IV. an aqueous dispersion of 10 parts by weight of a compound I according to the invention, 25 parts by weight of cyclohexanol, 55 parts by weight of a petroleum fraction of boiling point from 210° to 280° C., and 10 parts by weight of the addition product of 40 mol of ethylene oxide to 1 mol of castor oil;

V. a mixture, ground in a hammer mill, of 80 parts by weight, preferably of a solid compound I according to the invention, 3 parts by weight of the sodium salt of diisobutylnaphthalene-2-sulfonic acid, 10 parts by weight of the sodium salt of a lignosulfonic acid from a sulfite waste liquor and 7 parts by weight of powdered silica gel; a spray liquor is obtained by finely dispersing the mixture in water;

VI. an intimate mixture of 3 parts by weight of a compound I according to the invention and 97 parts by weight of finely divided kaolin; this dusting composition contains 3% by weight of active compound;

VII. an intimate mixture of 30 parts by weight of a compound I according to the invention, 62 parts by weight of powdered silica gel and 8 parts by weight of liquid paraffin which has been sprayed onto the surface of this silica gel; this preparation gives the active compound good adhesion;

VIII. a stable aqueous dispersion of 40 parts by weight of a compound I according to the invention, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of a compound I according to the invention, 2 parts by weight of the calcium salt of dodecylbenzenesulfonic acid, 8 parts by weight of fatty alcohol polyglycol ether, 20 parts by weight of the sodium salt of a phenolsulfonic acid/urea/formaldehyde condensate and 50 parts by weight of a paraffinic mineral oil.

The novel compounds are distinguished by an outstanding activity against a broad spectrum of phytopathogenic fungi, in particular from the class of Deuteromycetes, Ascomycetes, Phycomycetes and Basidiomycetes. They are systemically active in some cases and can be employed as foliar and soil fungicides.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds are applied by treating the fungi or the seeds, plants, materials or the soil to be protected from fungal attack with a fungicidally effective amount of the active compounds.

They are applied before or after the infection of the materials, plants or seeds by the fungi.

The novel compounds are specifically suitable for the control of the following plant diseases:

*Erysiphe graminis* (powdery mildew) in cereals, *Erysiphe cichoracearum* and *Sphaerotheca fuliginea* on cucurbits, *Podosphaera leucotricha* on apples, *Uncinula necator* on vines, Puccinia species on cereals, Rhizoctonia species on cotton and grass, Ustilago species on cereals and sugar cane, *Venturia inaequalis* (scab) on apples, Helminthosporium species on cereals, *Septoria nodorum* on wheat, *Botrytis cinerea* (gray mold) on strawberries, vines, decorative plants and vegetables, *Cercospora arachidicola* on groundnuts, *Pseudocercosporella herpotrichoides* on wheat, barley, *Pyricularia oryzae* on rice, *Phytophthora infestans* on potatoes and tomatoes, Fusarium and Verticillium species on various plants, *Plasmopara viticola* on vines, Alternaria species on vegetables and fruit.

The novel compounds can also be employed in the protection of materials (preservation of wood), eg. against *Paecilomyces variotii*.

The fungicidal compositions in general contain from 0.1 to 95, preferably from 0.5 to 90, % by weight of active compound.

Depending on the type of effect desired, the application rates are from 0.025 to 2, preferably from 0.1 to 1, kg of active compound per ha.

In seed treatment, amounts of active compound of from 0.001 to 50 g, preferably 0.01 to 10 g, per kilogram of seed are in general needed.

The compositions according to the invention can also be present as fungicides together with other active compounds in the application form, eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediamine bisdithiocarbamate, tetramethylthiuram disulfide, ammonia complex of zinc N,N-ethylenebisdithiocarbamate, ammonia complex of zinc N,N'-propylenebisdithiocarbamate, zinc N,N'-propylenebisdithiocarbamate, N,N'-polypropylenebis (thiocarbamoyl) disulfide;

nitro derivatives, such as dinitro(1-methylheptyl)phenyl crotonate, 2-sec-butyl-4,6-dinitrophenyl-3,3-dimethylacrylate, 2-secbutyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b] quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1, 2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4- oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butyl-phenyl)-2-methylpropyl]-cis-2,6-dimethylmorpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, α-[2-(4-chlorophenyl)ethyl]-α-(1,1-dimethylethyl)-1H-1,2,4-triazole-1-ethanol, 1-[3-(2-chlorophenyl)-1-(4-fluorophenyl)oxiran-2-yl-methyl]-1H-1,2,4-triazole, and various fungicides, such as dodecylguanidine acetate, 3-[3-(3,5-dimethyl-2-oxycyclohexyl)-2-hydroxyethyl] glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methyl-silyl)methyl)-1H-1,2,4-triazole, strobilurins such as methyl E-methoximino[α-(o-tolyloxy)-o-tolyl]acetate, methyl E-2-{2-[6-(2-cyanophenoxy)pyrimidin-4-yloxy]phenyl}-3-methoxyacrylate, methyl E-methoximino[α-(2,5-dimethoxy)-o-tolyl]acetamide, anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl) aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acrylic acid morpholide.

Synthesis Example

The procedure given in the synthesis example below can be used with modification of the starting compound to obtain further representatives of the compounds I. The physical data of the correspondingly prepared products are given in Tables 4 and 5.

N-(Isopropoxycarbonyl)-L-valine(1-(β-naphthyl)ethyl) amide (compound No. 4.2 in Table 4)

13.3 g (65 mmol) of diethyl cyanophosphate were added to a solution of 14.2 g (65 mmol) of tert-butoxycarbonyl-L-valine and 13.6 g (65 mmol) of 1-amino-1-(β-naphthyl) ethane in 300 ml of tetrahydrofuran. The mixture was stirred at 0° C. for 1 hour and at 20° C. for 15 hours. The solvent was then removed and the residue was taken up using 300 ml of ethyl acetate. The organic phase was washed with 200 ml in each case of 5% strength by weight sodium hydroxide solution, 10% strength hydrochloric acid, 10% strength by weight sodium hydrogen carbonate solution and water, dried and concentrated. 18.0 g (49 mmol) of N-(tert-butoxycarbonyl)-L-valine(1-(β-naphthyl)ethyl)amide (m.p. 97° C.) remained.

50 ml of trifluoroacetic acid were added with cooling to 17.0 g (46 mmol) of this compound and the mixture was stirred at 0° C. for 1 hour. It was then warmed to 20° C., the trifluoroacetic acid was largely removed by distillation, the residue was taken up in 300 ml of dichloromethane and this was washed with 200 ml each of 2N sodium hydroxide solution, 5% strength by weight sodium hydrogen carbonate solution and water. After drying and concentrating the organic phase, 10.7 g (40 mmol) of L-valine (1-(β-naphthyl) ethyl)amide remained as a yellow viscous oil.

0.54 g (2.0 mmol) of this compound and 0.22 g (2.2 mmol) of triethylamine in 40 ml of toluene were treated at 0° C. with 0.24 g (2.1 mmol) of isopropyl chloroformate and the mixture was stirred at 20° C. for 15 hours. After removing the solvent, the residue was taken up using 50 ml of ethyl acetate and the solution was washed with 40 ml in each case of 10% strength by weight hydrochloric acid, 10% strength by weight sodium hydrogen carbonate solution and water. After drying the organic phase, the solvent was removed. 0.58 g (1.6 mmol) of the title compound remained as a colorless crystalline residue (m.p. 127° C.).

TABLE 4

$$R^1-O-\underset{\underset{O}{\|}}{C}-\underset{\underset{H}{|}}{N}-\underset{\underset{CH(CH_3)_2}{|}}{CH}-\underset{\underset{O}{\|}}{C}-\underset{\underset{H}{|}}{N}-\underset{\underset{X}{|}}{CH}-(CH_2)_n-\text{[naphthyl]}-R^6$$

| No. | $R^1$ | X | n | $R^6$ | m.p. (°C.) IR (cm$^{-1}$) |
|---|---|---|---|---|---|
| 4.1 | C(CH$_3$)$_3$ | CH$_3$ | 0 | H | 97 |
| 4.2 | CH(CH$_3$)$_2$ | CH$_3$ | 0 | H | 127 |
| 4.3 | CH(CH$_3$)(C$_2$H$_5$) | CH$_3$ | 0 | H | 134–142 |
| 4.4 | C(CH$_3$)$_3$ | CH$_3$ | 0 | 6-CH$_3$ | 118–21 |
| 4.5 | CH(CH$_3$)$_2$ | CH$_3$ | 0 | 6-CH$_3$ | 175–88 |
| 4.6 | CH(CH$_3$)C$_2$H$_5$ | CH$_3$ | 0 | 6-CH$_3$ | 168–76 |
| 4.7 | C(CH$_3$)$_3$ | CH$_3$ | 1 | H | 65–70 |
| 4.8 | CH(CH$_3$)$_2$ | CH$_3$ | 1 | H | resin |
| 4.9 | CH(CH$_3$)$_2$ | CH$_3$ | 0 | 6-OCH$_3$ | resin |
| 4.10 | C(CH$_3$)$_3$ | CH$_3$ | 0 | 1-CH$_3$, 4-OMe | 75–7 |
| 4.11 | CH(CH$_3$)$_2$ | CH$_3$ | 0 | 1-CH$_3$, 4-OMe | 127–8 |

TABLE 5

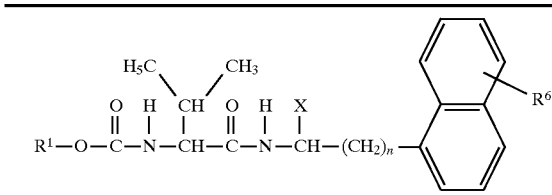

| No. | R₁ | X | n | R⁶ | m.p. (°C.) IR (cm⁻¹) |
|---|---|---|---|---|---|
| 5.1 | C(CH₃)₃ | CH₃ | 0 | H | 122–30 |
| 5.2 | CH(CH₃)₂ | CH₃ | 0 | H | 172–80 |
| 5.3 | CH(CH₃)C₂H₅ | CH₃ | 0 | H | 138–44 |
| 5.4 | C(CH₃)₃ | CH₃ | 0 | 4-Cl | 72–9 |
| 5.5 | CH(CH₃)₂ | CH₃ | 0 | 4-Cl | 196–8 |
| 5.6 | CH(CH₃)(C₂H₅) | CH₃ | 0 | 4-Cl | 166–9 |

Use examples

For the following tests, which are intended to show the fungicidal action of the compounds I, an emulsion was used which consisted to 10% by weight of the active compound, and to 80% by weight of a mixture of:
  70% by weight of cyclohexanol,
  20% by weight of Nekanil® LN (Lutensol® AP6, wetting agent having emulsifying and dispersant action based on ethoxylated alkylphenols) and
  10% by weight of Emulphor® EL (Emulan® EL, emulsifier based on ethoxylated fatty alcohols).
The desired active compound concentration was set by diluting the this emulsion with water.

*Plasmopara viticola*

Leaves of potted vines of the variety Müller-Thurgau were sprayed with aqueous spray liquor which contained 80% by weight of active compound and 20% by weight of emulsifier in the dry substance. In order to assess the duration of action of the active compounds, the plants were placed in a greenhouse for 8 days after the spray coating had dried on. Only then were the leaves infected with a zoospore suspension of *Plasmopara viticola* (vine Peronospora). The vines were first placed for 48 hours in a chamber containing water vapor-saturated air at 24° C. and then for 5 days in a greenhouse at from 20° to 30° C. After this time, the plants were placed in the moist chamber again for 16 hours to accelerate escape from the sporangiophore. The extent of fungal outbreak on the bottoms of the leaves was then assessed visually.

In this test, the leaves of plants which had been treated with an aqueous preparation containing 250 ppm or 63 ppm of in each case one of the compounds Nos. 4.1, 4.2, 4.3, 4.4, 4.5, 4.6, 4.7, 4.8, 4.9, 4.10, 5.2, 5.4, 5.5 and 5.6 showed, in the case of 250 ppm of active compound, a fungal attack on 0 to 5% of the leaf surface and, at 63 ppm, on 0 to 25% of the leaf surface. On the other hand, the leaves of the untreated plants were attacked to 80%.

*Phytophthora infestans*

Leaves of potted plants of the variety Große Fleischtomate were sprayed with aqueous spray liquor which contained 80% by weight of active compound and 20% by weight of emulsifier in the dry matter. After 24 hours, the leaves were infected with a zoospore suspension of the fungus Phytophthora infestans. The plants were then placed at from 16° to 18° C. in a chamber containing water vapor-saturated air. After 6 days, the attack on the untreated, but infected control plants had developed so severely that it was possible to assess the fungicidal activity of the substances visually.

In this test, the leaves of plants which had been treated with an aqueous preparation containing 250 ppm or 63 ppm of in each case one of the compounds Nos 4.1, 4.2, 4.3, 4.4, 4.5, 4.6, 4.7, 4.8, 4.9, 5.2, 5,4 and 5.6 showed a fungal attack on 0 to 15% of the leaf surface. On the other hand, the leaves of the untreated plants were attacked to 90%.

We claim:
1. A carbamoylcarboxamide of the general formula I

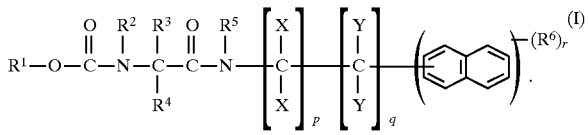

and its salts, where the variables have the following meanings:

R¹ is $C_1$–$C_8$-alkyl, $C_2$–$C_8$-alkenyl or $C_2$–$C_8$-alkynyl, it being possible for these radicals to be partially or completely halogenated and/or to carry one to three of the following groups: cyano, $C_1$–$C_4$-alkoxy, $C_1$–$C_4$-haloalkoxy, $C_1$–$C_4$-alkylthio, $C_1$–$C_4$-alkoxycarbonyl, $C_3$–$C_7$-cycloalkyl, $C_3$–$C_7$-cycloalkenyl, aryl, aryloxy and heteroaryl, it being possible for the cyclic and aromatic rings of these groups to carry one to three of the following substituents: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and heteroaryl, $C_3$–$C_7$-cycloalkyl or $C_3$–$C_7$-cycloalkenyl, it being possible for these radicals to be partially or completely halogenated and/or to carry one to three of the following groups: cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl, aryloxy and aryl-($C_1$–$C_4$)-alkyl, it being possible for the aromatic rings of these groups in turn to carry one to three of the following substituents: halogen, cyano, $C_1$–$C_4$-alkyl, $C_1$–$C_4$-alkoxy-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, a nonaromatic 4- to 8-membered ring which, as ring members, in addition to carbon can further contain one or two of the heteroatoms oxygen, sulfur and nitrogen, it being possible for the carbon atoms in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxy-carbonyl, aryl and aryloxy, and the second and any further nitrogen atom as a heteroatom in the ring carrying hydrogen or a $C_1$–$C_4$-alkyl group;

R² is hydrogen, or $C_1$–$C_8$-alkyl, or $C_3$–$C_7$-cycloalkyl which can be partially or completely halogenated;

R³ is $C_1$–$C_8$-alkyl, it being possible for this radical to carry one to three of the following groups: halogen, cyano, $C_1$–$C_4$-alkoxy, $C_1$–$C_4$-haloalkoxy, $C_1$–$C_4$-alkylthio and $C_1$–$C_4$-alkoxycarbon $C_3$–$C_7$-cycloalkyl or phenyl-($C_1$–$C_4$)-alkyl, it being possible for the rings of these radicals to carry one to three of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy;

R⁴ is hydrogen or one of the radicals R³ or $R^3$ and $R^4$, together with the C atom to which they are bonded, are a 4- to 8-membered ring which, as ring members, in addition to carbon can further contain one or two of the heteroatoms oxygen, sulfur and nitrogen, it being possible for the carbon atoms in the ring to carry one or two of the following groups: halogen, cyano, $C_1$–$C_4$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkoxycarbonyl, aryl and aryloxy, and nitrogen as a heteroatom carrying hydrogen or a $C_1$–$C_4$-alkyl group;

$R^5$ independently of these is one of the radicals $R^2$;

X independently of one another is hydrogen, $C_1$–$C_8$-alkyl and/or $C_2$–$C_8$-alkenyl, it being possible for these radicals to be partially or completely halogenated and/or to carry one to three of the following groups: cyano, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-alkoxycarbonyl, aryl and aryloxy;

Y independently of one another and of these is one of the radicals X;

p,q independently of one another are 0, 1 or 2, except that neither may both be 0;

$R^6$ is halogen, cyano, nitro, $C_1$–$C_8$-alkyl, $C_1$–$C_4$-alkoxyalkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio or a phenyl group bonded via oxygen or sulfur, which is unsubstituted or can carry one to three of the following substituents: halogen, $C_1$–$C_4$-alkyl or $C_1$–$C_4$-alkoxy, where $R^6$ for r>1 can be various radicals from those mentioned;

r is 0, 1, 2 or 3.

2. A process for preparing compounds of the general formula I as claimed in claim 1, which comprises reacting a carbamoylcarboxylic acid of the general formula II

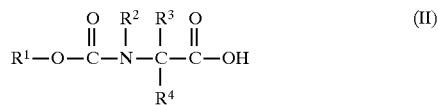

with an amine of the general formula III

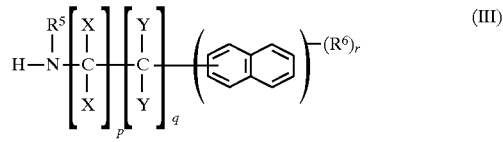

3. A process for preparing compounds of the general formula I as claimed in claim 1, which comprises a) converting a carbamoylcarboxamide of the general formula I

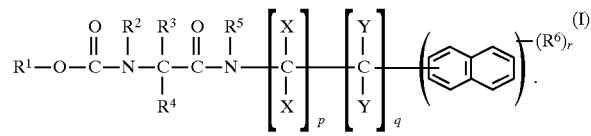

where the group $R^1$—O—(CO) is a protective group which can be removed in a manner known per se, to an amino acid amide IV

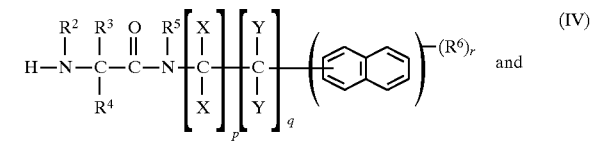

b) reacting the amino acid amide IV thus obtained with a chloroformic acid ester of the general formula V

in the presence of a base.

4. A composition suitable for controlling harmful fungi, containing at least one liquid or solid carrier and a fungicidally effective amount of at least one compound of the general formula I or a salt of I as claimed in claim 1.

5. A process for preparing compositions suitable for controlling harmful fungi, which comprises mixing a fungicidally effective amount of at least one compound of the general formula I or a salt of I as claimed in claim 1 and at least one inert liquid or solid carrier and, if desired, at least one adjuvant.

6. A method of controlling harmful fungi, which comprises treating the harmful fungi, their habitat or the plants, surfaces, materials or spaces to be kept free from them with a fungicidally effective amount of at least one compound of the general formula I or one of its salts as claimed in claim 1.

7. A method of controlling harmful fungi, which comprises treating the harmful fungi, their habitat or the plants, surfaces, material or spaces to be kept free from them with a fungicidally effective amount of at least one composition as claimed in claim 4.

* * * * *